US010499900B2

(12) United States Patent
Wade (10) Patent No.: US 10,499,900 B2
(45) Date of Patent: Dec. 10, 2019

(54) IMPLANT DEVICES AND SYSTEMS FOR STABILIZED FIXATION OF BONE AND SOFT TISSUE

(71) Applicant: Tensyn Medical, Inc., Seattle, WA (US)

(72) Inventor: Russell W. Wade, Laguna Niguel, CA (US)

(73) Assignee: TENSYN MEDICAL, INC., Seattle, WA (US)

( * ) Notice: Subject to any disclaimer, the term of this patent is extended or adjusted under 35 U.S.C. 154(b) by 578 days.

(21) Appl. No.: 14/666,095

(22) Filed: Mar. 23, 2015

(65) Prior Publication Data

US 2016/0089131 A1 Mar. 31, 2016

Related U.S. Application Data

(60) Provisional application No. 62/056,276, filed on Sep. 26, 2014, provisional application No. 62/108,503, filed on Jan. 27, 2015.

(51) Int. Cl.
*A61B 17/04* (2006.01)
*A61B 17/84* (2006.01)
*A61F 2/08* (2006.01)

(52) U.S. Cl.
CPC .......... *A61B 17/0401* (2013.01); *A61B 17/84* (2013.01); *A61B 2017/0404* (2013.01);
(Continued)

(58) Field of Classification Search
CPC ........ A61B 17/84–848; A61B 17/8665; A61B 17/8695; A61B 17/0401; A61B 2017/867–868; A61B 2017/0404; A61B 2017/042–0425; A61B 2017/044–0453; A61B 2017/0458; A61B 2017/0464;
(Continued)

(56) References Cited

U.S. PATENT DOCUMENTS 5,921,986 A 7/1999 Bonutti
6,159,234 A * 12/2000 Bonutti .............. A61B 17/0487
606/148

(Continued)

OTHER PUBLICATIONS

International Search Report and Written Opinion in related PCT Application US2015/52373. International Filing date Sep. 25, 2015.

*Primary Examiner* — Jonathan A Hollm
(74) *Attorney, Agent, or Firm* — Donald E. Stout; Stout, Uxa & Buyan, LLP (57) ABSTRACT

An implant system for providing stabilized fixation of tissue includes a button having a slot, a band threaded through the slot, and a lock including a member having a slot for receiving an end of the band and a movable member for clamping the band in place. The movable member is movable between an open position and a locking position. The lock is a plug assembly which includes a flange. The slot is disposed in the flange. The movable member is a cap which is movable between clamping and non-clamping orientations relative to the flange. The plug assembly further comprises a screw for moving the cap between its clamping and non-clamping orientations relative to the flange. The flange is a portion of a plug, which plug further includes a boss extending from one side of the flange.

14 Claims, 6 Drawing Sheets

(52) U.S. Cl.
CPC . *A61B 2017/044* (2013.01); *A61B 2017/0453* (2013.01); *A61F 2/0811* (2013.01); *A61F 2002/0852* (2013.01); *A61F 2002/0882* (2013.01)

(58) Field of Classification Search
CPC ........... A61B 2017/0453; A61F 2/0811; A61F 2002/0817–0888
See application file for complete search history.

(56) References Cited

U.S. PATENT DOCUMENTS

| | | | |
|---|---|---|---|
| 6,221,107 B1* | 4/2001 | Steiner ................. | A61F 2/0811 623/13.13 |
| 7,713,221 B1 | 5/2010 | Weber et al. | |
| 7,833,244 B2 | 11/2010 | Cerundolo | |
| 7,875,057 B2* | 1/2011 | Cook ...................... | A61D 1/00 128/898 |
| 8,221,455 B2 | 7/2012 | Shumas et al. | |
| 8,303,591 B1 | 11/2012 | Foerster et al. | |
| 8,398,678 B2 | 3/2013 | Baker et al. | |
| 8,425,554 B2 | 4/2013 | Denove et al. | |
| 8,512,376 B2 | 8/2013 | Thornes | |
| 8,591,578 B2 | 11/2013 | Albertorio | |
| 8,771,316 B2 | 7/2014 | Denham | |
| 8,932,331 B2 | 1/2015 | Kaiser et al. | |
| 9,005,287 B2 | 4/2015 | Stone | |
| 9,101,426 B2 | 8/2015 | Forderer et al. | |
| 2003/0236555 A1 | 12/2003 | Thornes | |
| 2004/0097939 A1 | 5/2004 | Bonutti | |
| 2005/0192631 A1* | 9/2005 | Grafton ............ | A61B 17/06166 606/228 |
| 2007/0016208 A1* | 1/2007 | Thornes ................. | A61B 17/68 606/331 |
| 2008/0275553 A1* | 11/2008 | Wolf .................. | A61B 17/0401 623/13.14 |
| 2011/0313435 A1 | 12/2011 | Aldridge et al. | |
| 2012/0123474 A1 | 5/2012 | Zajac | |
| 2012/0130492 A1* | 5/2012 | Eggli ........................ | A61F 2/08 623/13.14 |
| 2015/0359530 A1* | 12/2015 | Moore ............... | A61B 17/0401 606/232 |

* cited by examiner

IMPLANT DEVICES AND SYSTEMS FOR STABILIZED FIXATION OF BONE AND SOFT TISSUE

This application claims the benefit under 35 U.S.C. 119(e) of the filing date of Provisional U.S. application Ser. No. 62/056,276, entitled Implant Device for Stabilized Fixation of Bone and Soft Tissue, filed on Sep. 26, 2014, and also claims the benefit under 35 U.S.C. 119(e) of the filing date of Provisional U.S. Application Ser. No. 62/108,503, entitled Implant Device for Stabilized Fixation of Bone and Soft Tissue, filed on Jan. 27, 2015.

This application is also related to U.S. application Ser. No. 14/449,878, entitled Implant Device and System for Stabilized Fixation of Bone and Soft Tissue, filed on Aug. 1, 2014, now published as U.S. Published Application No. 2015/0039029, and commonly assigned herewith. All of the foregoing applications are expressly incorporated herein by reference, in their entirety.

BACKGROUND OF THE INVENTION

A syndesmosis is a slightly movable articulation where the contiguous bony surfaces are united by an interosseous ligament. If the syndesmosis is separated because of bone fracture, surgeons will sometimes fix the relevant bones together with a syndesmotic screw. The screw inhibits normal movement of the bones and, thereby, the corresponding joint or joints. When the natural articulation is healed, the screw may be removed.

Syndesmosis screws have significant problems, including loosening, breakage, the need for removal, and late diastasis. The present invention has been developed to address these problems, by providing a low profile implant device intended to facilitate stabilized fixation of tissues, including bone and soft tissue to bone, for syndesmosis repair, as well as other applications.

SUMMARY OF THE INVENTION

The inventive implant system comprises a low profile implant device intended to provide stabilized fixation of tissue to facilitate syndesmosis repair. These tissues include bone and soft tissue to bone. The inventive system can provide stabilized fixation for bone fractures, osteotomies, and arthrodesis, plus soft tissue to bone attachment. The system design applies a restorative fixation force across the tissue segments to stabilize them. The rigidity and compliant nature of the inventive implant provides rigid and consistent fixation during the healing phase.

The implant is delivered through a pre-drilled hole through the tibia and fibula by means of a guide needle delivery, exiting the skin opposite the initial insertion site. The flat band is secured to the bone by pulling the narrow button through both the tibia and fibula bones and then toggled into position to create tension across the two segments. Once the button is secure against the bone, the suture attached to the needle can be cut and removed from the operative site. Pulling the flat suture tails against the lock at the initial insertion site will tension the band and bone segments into place. The inventive implant system offers syndesmosis repair with a knotless closure.

The inventive implant is supplied as a one-size-fits-all single-use sterile implant. A kit containing one or more inventive implants, packaged for use in a single procedure, also contains a band of the type described in prior U.S. application Ser. No. 14/449,878, already expressly incorporated herein by reference, in its entirety.

The inventive implant system and method are intended for use as an adjunct in fracture repair involving metaphyseal and periarticular small bone fragments where screws are not indicated, and as an adjunct in external and intramedullary fixation systems involving plates and rods, with fracture braces and casting. Specifically, the inventive implant is intended to provide fixation during the healing process following a syndesmotic trauma, such as fixation of syndesmosis (syndesmosis disruptions) in connection with Weber B and C ankle fractures.

Although the inventive implant system is targeted to repair syndesmosis injuries of the ankle, it has application to other suitable types of repair as well, including, for example the shoulder.

In operation, the implant system is placed after pre-drilling by the practitioner. Standard drill, drill bits, and drill guides typically associated with orthopedic surgery are used to conduct the procedure. After appropriate reduction of the tibia and fibula bones, the operative technique is to A) first pass the guide needle through and out of the medial skin, B) pull through the lead, "narrow" button that is attached to the cortical surface so that it slips across and engages onto the medial tibial cortex, and D) pull on the implant suture tails to tighten and lock the proximal button.

After passing the distal button through the pre-drilled holes by means of the pass-through needle, reduction of the ankle joint is achieved by applying tension to the band and the metallic button. Fixation forces are activated by pulling on the suture tails after removing the pass-through needle and pass-through sutures and using a screwdriver to tighten the screw. A hand-held stainless steel tensioner instrument is considered if higher tension levels are necessary to meet physiological requirements.

The inventive implant is a sterile device using common implant materials, such as stainless steel or titanium, or other suitable materials. Bio-absorbable materials may also be considered for the implant system and the narrow button mechanism. The flat band is constructed of polyester suture material, or a suitable Ultra-High Molecular Weight Polyethylene (UHMWPE). Materials used in the deployment of the implant comprise suture material, a stainless steel guide needle, and a plastic protective cap.

Possible associated instrumentation, such as a stainless steel hand-held instrument tensioner or anti-rotation tool may be used if the mechanism requires higher levels of tensioning.

More particularly, in one aspect of the invention there is provided an implant system for stabilized fixation of tissue. The system comprises a button having a slot, a band threaded through the slot, and a lock comprising a member having a slot for receiving an end of the band and a movable member for clamping the band in place. The movable member is movable between an open position and a locking position. The button comprises a pair of slots and the band is threaded through each of the pair of slots in sequence, so that the band is wrapped around a portion of the button separating the two slots. The band, in present embodiments, is formed of suture material, such as a length of flat suture material, which can be threaded through the pair of slots of the button and through the slot of the lock so that between the button and the lock the band comprises the length of suture doubled over itself.

The lock comprises a plug assembly which includes a flange. The slot is disposed in the flange. The movable member comprises a cap which is movable between clamping and non-clamping orientations relative to the flange. The plug assembly further comprises a screw for moving the cap between its clamping and non-clamping orientations relative to the flange.

A second slot is provided in the flange, so that the band may be threaded through the first slot in the flange, cross a surface of the flange, and then extend through the second slot in the flange, thereby securing the band to the flange. The flange comprises a portion of a plug, the plug further comprising a boss extending from one side of the flange.

When the band is threaded through the slots of the flange, each end of the band extends along a length of the boss. Accordingly, the boss may comprise flat surfaces disposed along its length for accommodating the band ends extending therealong.

The implant system further comprises a suture tether attached to the button, and further comprises a guide needle attached to the suture tether, for assisting in positioning the implant as desired at a procedural site.

In another aspect of the invention, there is provided a lock for use in an implant system for stabilized fixation of tissue. The lock comprises a member having a slot for receiving an end of a band and a movable member for clamping the band in place. The movable member is movable between an open position and a locking position. The lock comprises a plug assembly which includes a flange. The slot is disposed in the flange. The movable member comprises a cap which is movable between clamping and non-clamping orientations relative to the flange. The plug assembly further comprises a screw for moving the cap between its clamping and non-clamping orientations relative to the flange.

A second slot is provided in the flange, so that a band may be threaded through the first slot in the flange, cross a surface of the flange, and then extend through the second slot in the flange, thereby securing the band to the flange. The flange comprises a portion of a plug, the plug further comprising a boss extending from one side of the flange.

When a band is threaded through the slots of the flange, each end of the band extends along a length of the boss. Accordingly, the boss may comprise flat surfaces disposed along its length for accommodating the band ends extending therealong.

In yet another aspect of the invention, there is disclosed a method for effecting repair of tissue using a tissue fixation band apparatus comprising a lock, a button, and a suture band, under tension, extending between the lock and the button. The inventive method comprises a step of pulling the button through a hole extending through the tissue to be repaired, until it exits a distal surface of the tissue and engages the distal surface of the tissue. Then, the suture band is pulled on each end to locate the lock in position on a proximal surface of the tissue. Additional steps include applying tension to free ends of the suture band exiting from the lock of the fixation band apparatus to tension the suture band to a desired level and causing a movable clamping member within the lock to move to a locking position, to thereby engage the lock and clamp the suture band in place at the desired tension level.

More specifically, the causing step comprises tightening a screw to cause the movable clamping member to move to its locking position. The lock comprises a plug assembly and the movable clamping member comprises a cap.

The invention, together with additional features and advantages thereof, may best be understood by reference to the following description taken in conjunction with the accompanying illustrative drawings.

DESCRIPTION OF THE PREFERRED EMBODIMENT

Figures 1, 2A, 2B:
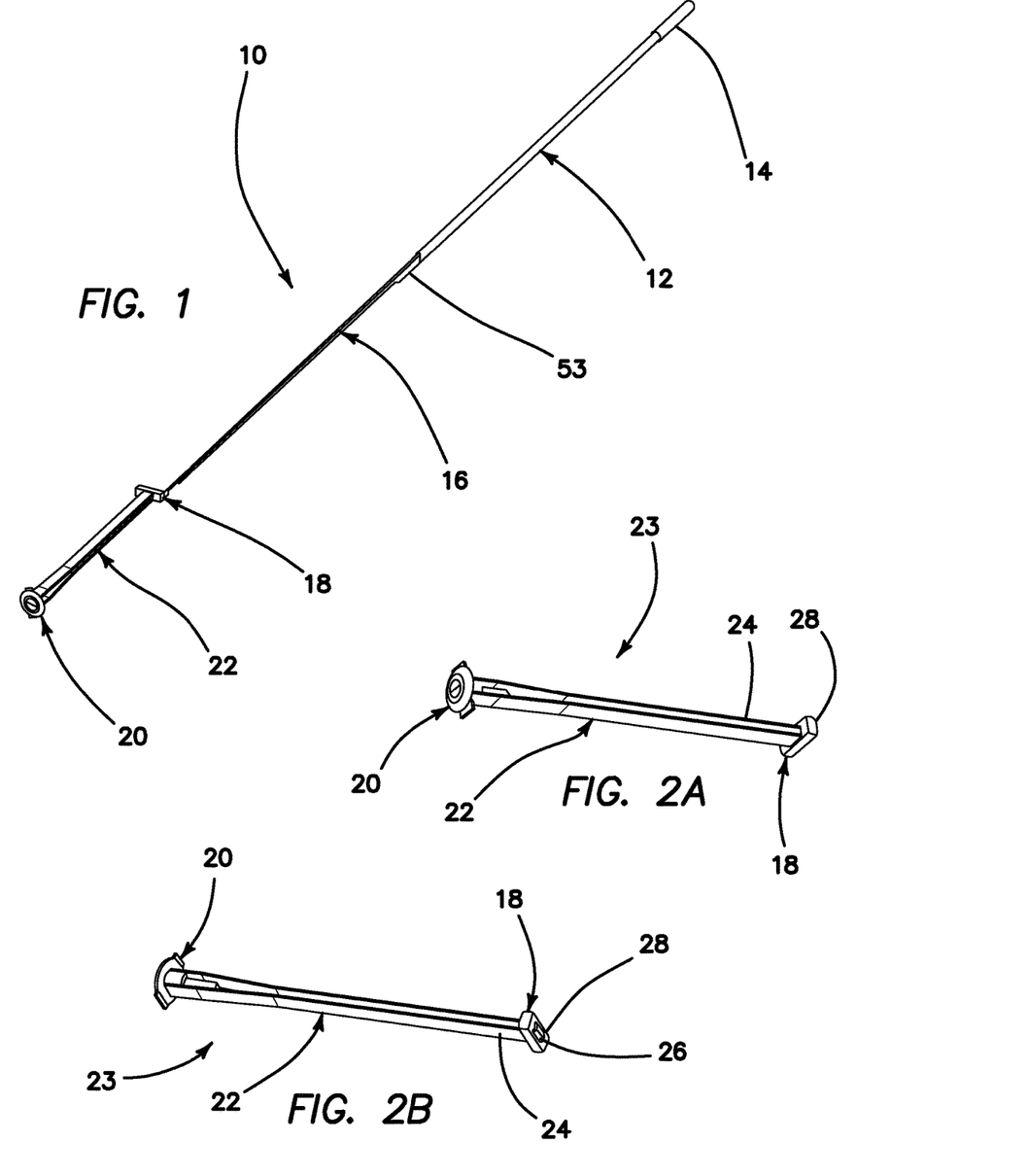
FIG. 1 is an isometric view of an implant system constructed in accordance with the principles of the present invention.
FIG. 2A is a top isometric view of the assembly of FIG. 1, with suture tether, guide needle and cap excluded for clarity.
FIG. 2B is a bottom isometric view, similar to FIG. 2A, of the assembly of FIG. 1.

Referring more particularly to the drawings, there is shown in FIG. 1 an implant system 10 for providing stabilized fixation of tissues. The system 10 includes a guide needle 12, a protective cap 14 on one end of the needle 12, to protect the sharp tip of the needle and prevent needle sticks, a suture tether 16 attached at one end to an opposed second end of the guide needle 12, a button 18 attached to an opposed second end of the suture tether 16, a plug assembly 20, and a band 22 joined to and extending between the button 18 and plug assembly 20. Although the dimensions of these components may be varied considerably, within the scope of the invention, in one particular embodiment, the total length of the system is approximately 14 inches, with the length of the band 22, plug 20, and button 18 portion of the system totaling about 3.0 inches, the length of the suture tether 16 being about 5.0 inches, and the length of the guide needle 12 and cap 14 being about 6.0 inches. By itself, in one embodiment, by way of example only, the cap is about 0.77 inches in length.

FIGS. 2A and 2B illustrate an implant assembly 23 of the implant system shown in FIG. 1. Notably, the button 18 may be manufactured from a surgical stainless steel or other suitable biocompatible material, such as 316 LVM stainless steel, titanium, or other suitable materials, such as bio-absorbables. Suture 24, comprising the suture band 22, is laced through slots 26 in a frame 28 forming the button 18, prior to use. As noted above, the band 22 is comprised of suture 24, which is, in particular embodiments, a woven polyester suture made from PET (polyethylene terephthalate), the same polyester as most commercially available sutures, or a suitable UHMWPE. The band may be polycoated or uncoated. In one embodiment, the suture 24 is provided in an overall length of 36 inches. The suture length between the narrow button 18 and the plug assembly 20 is nominally set to 3 inches, and is adjustable by the practitioner per the anatomical requirements of the patient.

It is noted that the narrow button 18 is small enough to pass through a hole 42 through the tibia and fibula (discussed below), with a suture band attached and a tether suture an guide needle attached. The slots 26 in the button 18 are large enough to lace the suture band therethrough. The edges of the slots are smooth, with an internal radius to prevent band breakage during loading. The thickness of the narrow button is just enough to withstand ankle loads. The sides of the narrow button 18 are contoured in the shape of the hole 42 to provide maximum strength and clearance through the holes in the tibia and fibula.

Figure 4A:
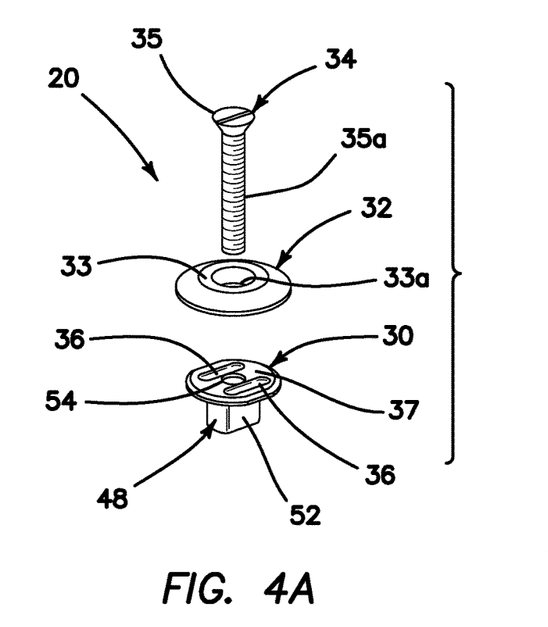
FIG. 4A is a top exploded isometric view of the plug assembly, including plug, screw, and cap components of the inventive system.
Figure 4B:
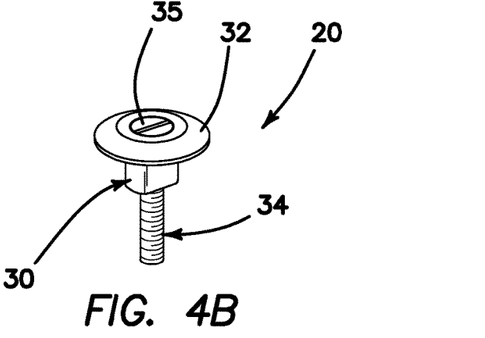
FIG. 4B is a top isometric view of the plug assembly shown in FIG. 4A.
Figure 4C:
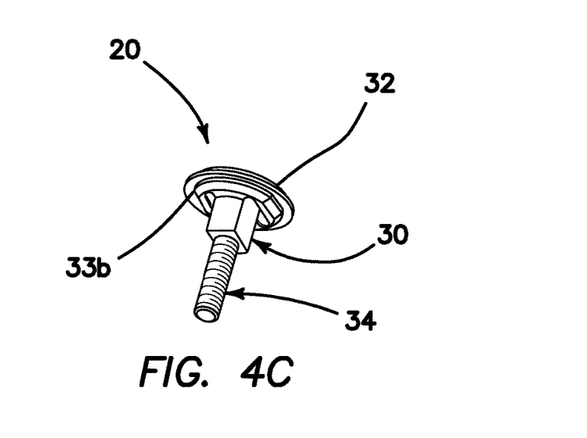
FIG. 4C is a bottom isometric view of the plug assembly shown in FIGS. 4A and 4B.
Figure 5A:
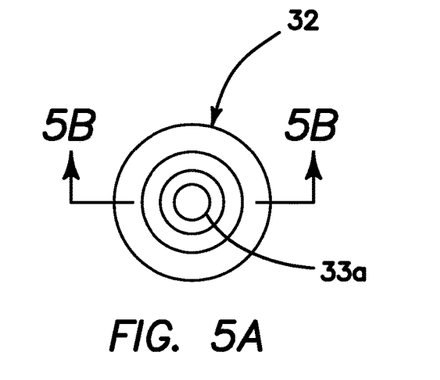
FIG. 5A is a top view of the cap component of the present invention.
Figure 5B:
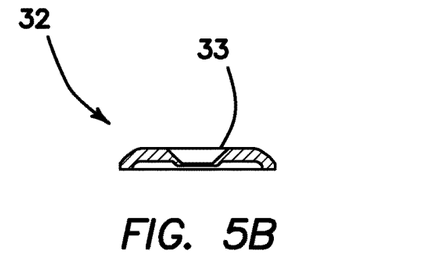
FIG. 5B is a cross-sectional view taken along lines 5B-5B of FIG. 5A.
Figure 5C:
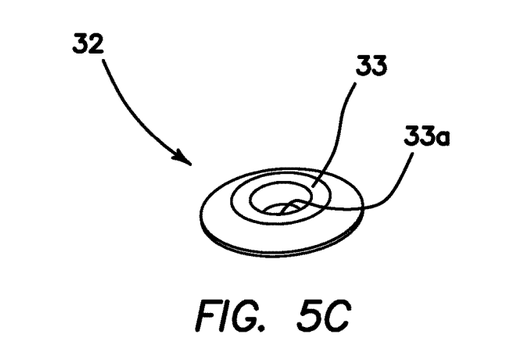
FIG. 5C is a top isometric view of the cap of FIGS. 5A and 5B.
Figure 5D:
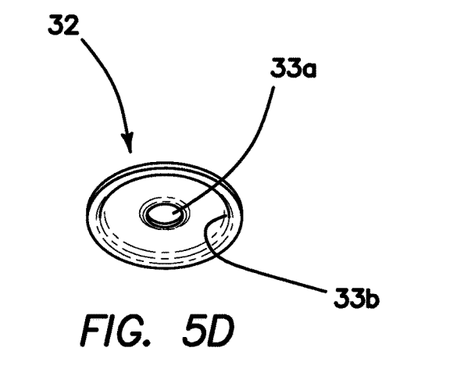
FIG. 5D is a bottom isometric view of the cap of FIGS. 5A-5C.
Figure 5E:
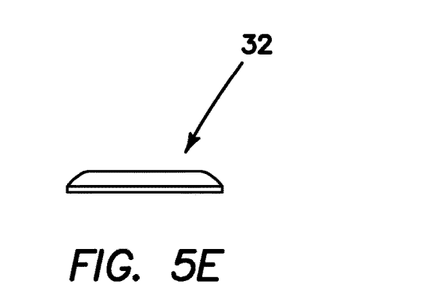
FIG. 5E is a side view of the cap of FIGS. 5A-5D.
Figure 5F:
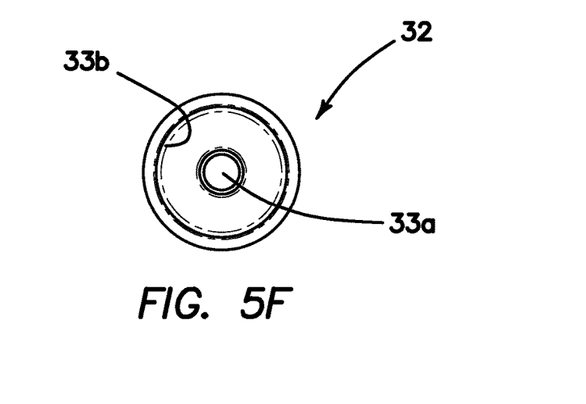
FIG. 5F is a bottom view of the cap of FIGS. 5A-5E.
Figure 6A:
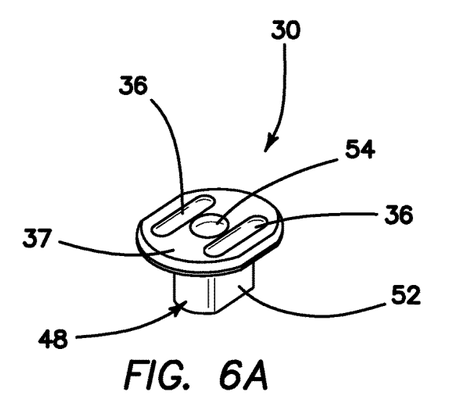
FIG. 6A is a top isometric view of the plug component of the present invention.
Figure 6B:
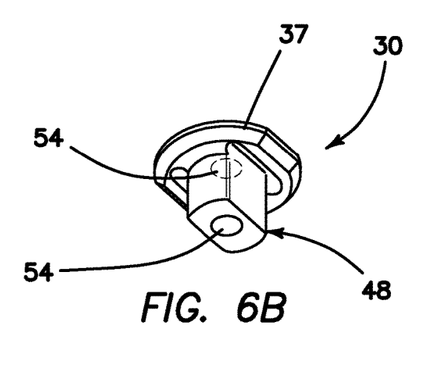
FIG. 6B is a bottom isometric view of the plug component of FIG. 6A.
Figure 6C:
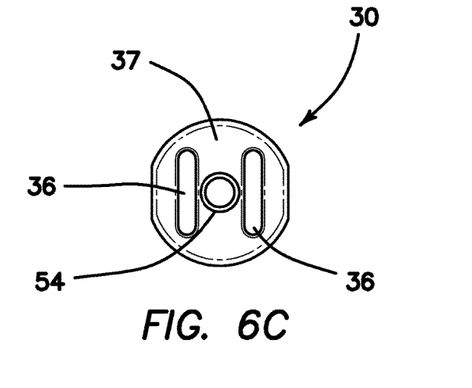
FIG. 6C is a top view of the plug component of FIGS. 6A-6B.
Figure 6D:
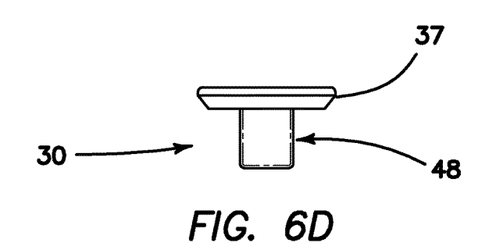
FIG. 6D is a side view of the plug component of FIGS. 6A-6C.
Figure 6E:
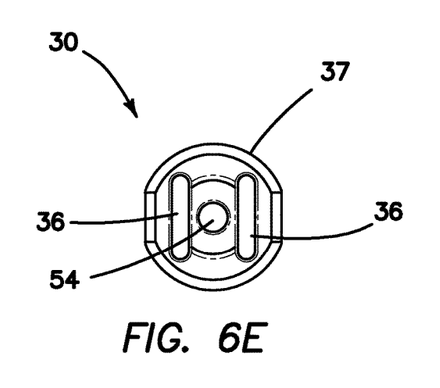
FIG. 6E is a bottom view of the plug component of FIGS. 6A-6D.

Now with reference more particularly to FIGS. 4A-4C, the plug assembly 20 is shown in greater detail. The plug assembly 20 comprises three main components, namely, a plug 30, a cap 32, and a screw 34. The entire assembly 20 is preferably made of 316 LVM stainless steel or titanium or other suitable biocompatible materials, such as bio-absorbables. The suture 24 is laced through slots 36 in a flange 37 of the plug 30 and the two ends of the suture 24 are tensioned. When the cap 32 is secured with the captive screw 34, as shown in FIGS. 4B and 4C, the plug assembly 20 is in a locked orientation.

The screw is of sufficient strength to withstand the loads of tensioning the implant assembly 23 and to endure subsequent stresses after implantation. It preferably has a flat head 35 to allow the fastener to lie flush with the cap 32, and additionally has a cross feature to allow for a standard matching driver. The length of the screw threads 35a is sufficient to withstand the required loads and provide adjustment of the suture, plug, and cap during installation. The cap 32 has a countersink feature 33 for receiving the flat head 35 of the screw 34, as well as an undersized through hole 33a to keep the screw 34 captive. The cap 32 further has a round body with smooth radii edges to aid in concealing the plug assembly 20 beneath the patient's skin. An internal counter bore 33b provides clearance for the plug flange 37, as well as a load bearing surface for the suture band 22. An internal edge radius assists in tensioning the suture and an additional contact surface traps the suture between the cap edge and the bone.

The plug flange 37 is thin, but of sufficient thickness to withstand the stresses of the ankle and thin enough to prevent excessive protrusion. The plug also comprises a boss 48, extending from the flange 37, which is long enough to allow for sufficient thread engagement. Flats 52 on the boss 48 act as clearance between the plug and bone to allow the suture to pass therebetween. A hole 54 in the plug flange accommodates the screw 34.

Again referring to FIG. 1, the guide needle 12 may be made of 302 stainless steel, such as that used for most surgical needles, although other suitable biocompatible materials may be used as well. The needle, in the illustrated embodiment, is 6 inches in length and has a diameter of 0.078 inches. A 5 inch polyester (PET) suture is used to attach the needle 12 and the narrow button 18, the suture being attached to the needle 12 via an eyelet 53. After placement of the narrow button 18, the suture and the straight needle are discarded.

In operation, the implant assembly 23 is delivered using similar techniques to other syndesmosis repair devices. In one such approach, a 3.6 mm hole 42 is pre-drilled through the cortices of the tibia 38 and fibula 40 (FIG. 3) from the open lateral side 44, for the purpose of repairing a separated syndesmosis 46. After appropriate reduction of the tibial and fibula bones, the straight guide needle 12 of the implant system 10 is passed through the drilled hole in the tibia and fibula and through the skin on the medial side, taking care to register the narrow button 18 into the pre-drilled hole 42. Tension is applied to the suture tether 16 to pull the narrow button 18 through both the fibula and tibia bones to the medial side, at which point the button 18 is toggled into position, lying flat against the medial cortex of the tibial bone 38, as shown. This creates tension across the two bone segments. At this juncture, the suture tether 16 and needle 12 are removed and discarded. Pulling the suture band 22 lightly on each end brings the lateral plug 30 to rest, flat on the fibula 40, as shown. Using a driver, the screw 34 is rotated within the cap 32 until the screw and cap are tight. The suture ends are then cut. The result is a syndesmosis repair with a knotless closure.

Figures 7A, 7B:
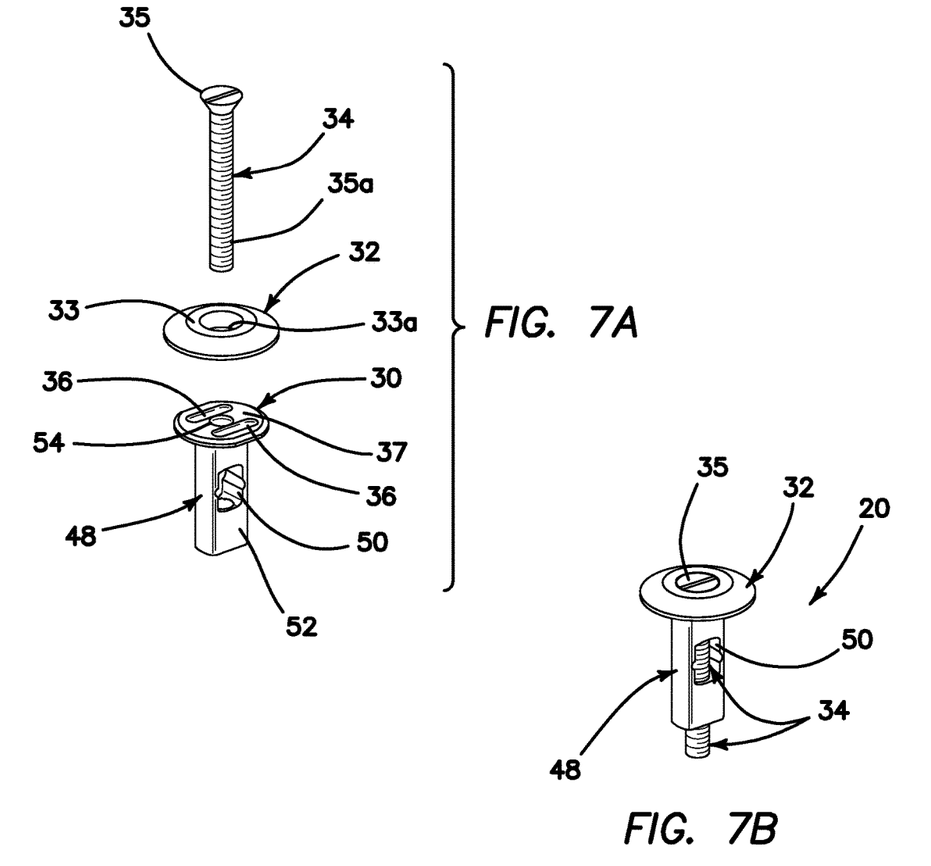
FIG. 7A is a top exploded view of a modified embodiment of the plug assembly, including plug, screw, and cap components of the present invention.
FIG. 7B is a top isometric view of the plug assembly of FIG. 7A.
Figure 7C:
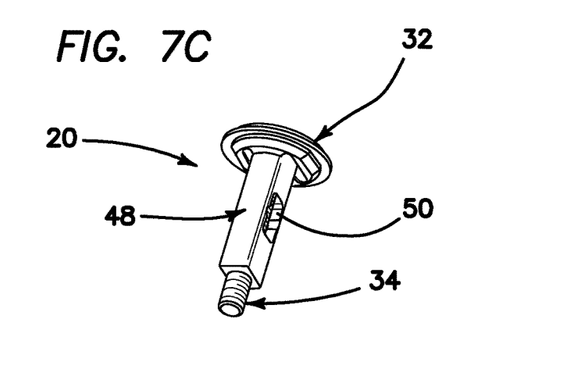
FIG. 7C is a bottom isometric view of the plug assembly of FIGS. 7A-7B.
Figure 8A:
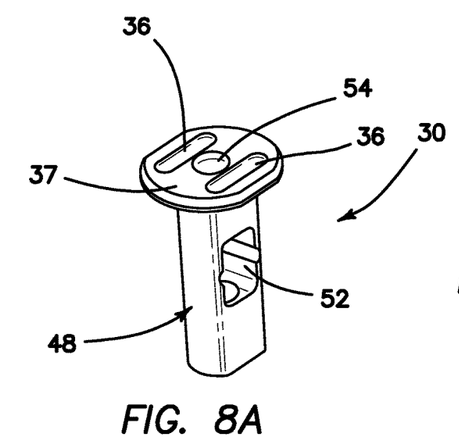
FIG. 8A is a top isometric view of the plug component of the assembly shown in FIGS. 7A-7C.
Figure 8B:
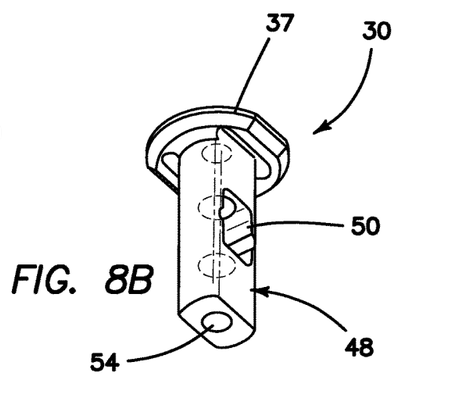
FIG. 8B is a bottom isometric view of the plug component shown in FIG. 8A.
Figure 8C:
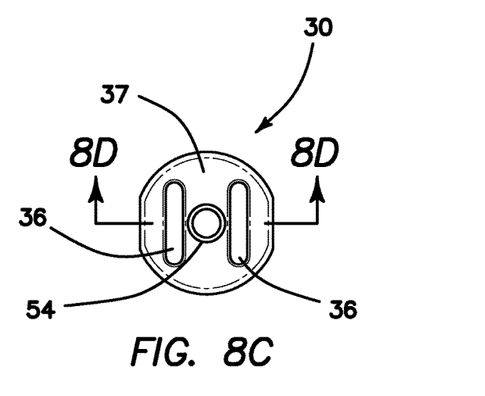
FIG. 8C is a top view of the plug component shown in FIGS. 8A-8B.
Figure 8D:
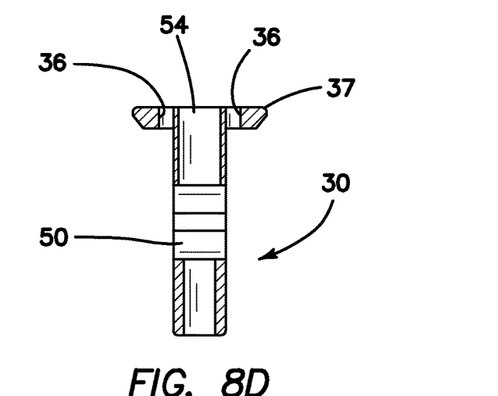
FIG. 8D is a cross-sectional view taken along lines 8D-8D of FIG. 8C.
Figure 8E:
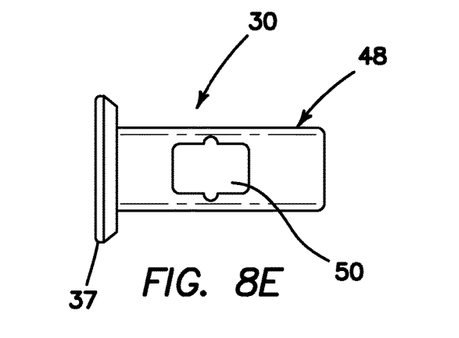
FIG. 8E is a side view of the plug component shown in FIGS. 8A-8D.
Figure 8F:
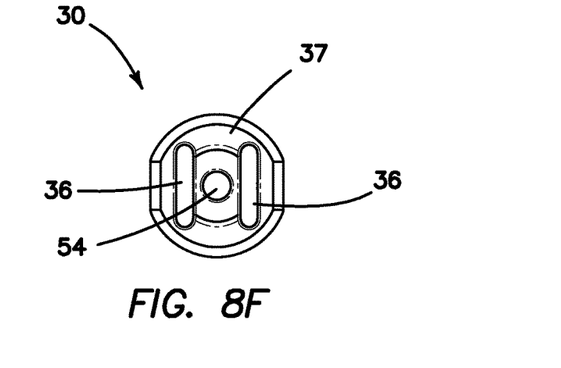
FIG. 8F is a bottom view of the plug component shown in FIGS. 8A-8E.

FIGS. 7 and 8 illustrate an alternative embodiment of the plug assembly 20, which is particularly useful for providing stabilized fixation in an ACL repair, or other repairs where a separate anchor location is needed. The major difference between the FIG. 7 embodiment and that shown in FIGS. 1-6 is that the boss 48 of the FIG. 7 embodiment is substantially greater in length than the boss 48 of the FIG. 1-6 embodiment, and includes an aperture 50 extending laterally therethrough. In the ACL repair scenario, for example, a blind hole in the bone is drilled, the plug 30 is inserted into the hole, and, as the screw 34 is tightened, the plug body, particularly the boss 48, expands and compresses against the bone defining the blind hole, thereby anchoring the plug in place.

Figure 3:
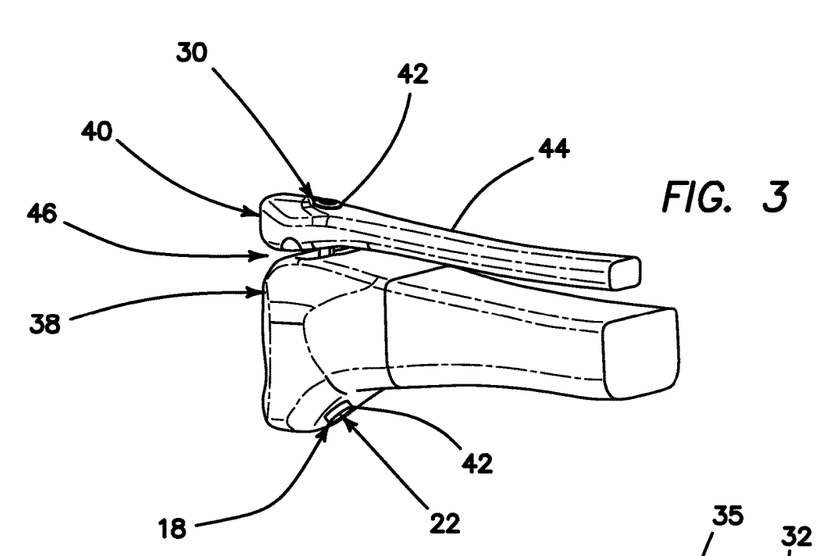
FIG. 3 is an isometric view of the inventive implant installed with a tibia and fibula, according to one particular method of the present invention.

It should be noted, however, that the FIG. 7 embodiment of the plug assembly 20 may be used in the procedure shown in FIG. 3, if desired.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. An implant system for stabilized fixation of tissue, comprising:
   a button comprising a pair of slots;
   a band having a length and being formed of suture material along its entire length which is adapted to be threaded through each of the pair of slots in sequence, so that the suture material is wrapped around a portion of the button separating the two slots; and
   a lock comprising a plug assembly, the plug assembly comprising a plug, the plug further comprising a horizontally disposed planar flange which lies across an entire width of the plug, and having a horizontally disposed slot disposed in the flange, the suture material also being adapted to be threaded through the slot disposed in the flange so that between the button and the lock the band comprises said length of suture material doubled over itself along an entire distance between the lock and the button, the plug assembly further comprising a fastener which is movable between clamping and non-clamping orientations relative to the flange;
   wherein the plug assembly further comprises a cap which is movable with the fastener between the fastener's clamping and non-clamping orientations relative to the flange, the cap having a center opening and being adapted to engage the flange of the plug, the cap center opening being adapted for receiving the fastener therethrough.

2. The implant system as recited in claim 1, wherein the suture material is a length of flat suture material.

3. The implant system as recited in claim 1, and further comprising a second slot in the flange, so that the band may be threaded through the first slot in the flange, cross a surface of the flange, and then extend through the second slot in the flange, thereby securing the band to the flange.

4. The implant system as recited in claim 3, wherein the plug further comprises a boss extending from one side of the flange.

5. The implant system as recited in claim 4, wherein when the band is threaded through the slots of the flange, each end of the band extends along a length of the boss.

6. The implant system as recited in claim 5, wherein the boss comprises flat surfaces disposed along its length for accommodating the band ends extending therealong.

7. The implant system as recited in claim 1, and further comprising a suture tether attached to the button.

8. The implant system as recited in claim 7, and further comprising a guide needle attached to the suture tether.

9. The implant system as recited in claim 1, wherein the fastener comprises a screw.

10. The implant system as recited in claim 9, wherein the screw has a flat head.

11. The implant system as recited in claim 1, wherein the horizontally disposed slot extends across more than half of the entire width of the plug.

12. A method for effecting repair of tissue using a tissue fixation band apparatus comprising a lock, a button, and a suture band, under tension, extending between the lock and the button, the suture band having first and second ends, comprising:
   pulling the button through a hole extending through the tissue to be repaired, until it exits a distal surface of the tissue and engages the distal surface of the tissue;
   pulling the suture band on each of the first and second ends to locate the lock in position on a proximal surface of the tissue;
   applying tension to the first and second ends of the suture band exiting from the lock of the fixation band apparatus to tension the suture band to a desired level; and
   causing a fastener within the lock to move to a clamping position, to thereby engage the lock and clamp the suture band in place at the desired tension level, wherein the suture band comprises a length extending between the lock and the button, the suture band comprising doubled-over suture along said length, in its entirety, the causing step comprising tightening the fastener to cause a cap having a lower clamping surface to move to a locking position;
   wherein the lock comprises a plug assembly having a horizontally disposed flange comprising an upper end of a plug and extending across an entire width of the plug, the cap moving downwardly into engagement with the flange when the causing step is performed, the cap preventing the suture band from moving through slots in the flange when the cap is in the locking position.

13. The method as recited in claim 12, wherein the fastener comprises a screw.

14. The method as recited in claim 13, wherein the screw has a flat head.

* * * * *